(12) United States Patent
Gao

(10) Patent No.: US 8,985,593 B1
(45) Date of Patent: Mar. 24, 2015

(54) SELF-LOCKING INTERNAL ADAPTER FOR D-SHAPED ORTHOPEDIC ADJUSTMENT TOOLS

(75) Inventor: Hua Gao, Fox Point, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 0 days.

(21) Appl. No.: 13/183,293

(22) Filed: Jul. 14, 2011

(51) Int. Cl.
  *B23B 31/16* (2006.01)

(52) U.S. Cl.
  USPC ............................... 279/75; 279/74; 606/79

(58) Field of Classification Search
  USPC .................. 279/22, 30, 74, 75, 82, 904, 905; 606/79, 80, 86 R, 96; 81/437–439, 81/177.85
  See application file for complete search history.

(56) References Cited

U.S. PATENT DOCUMENTS

| | | | |
|---|---|---|---|
| 1,307,937 A | 6/1919 | Straub | |
| 2,289,583 A | 7/1942 | Melone | |
| 3,521,895 A * | 7/1970 | Smith | 279/22 |
| 3,967,830 A * | 7/1976 | Smith | 279/16 |
| 5,741,263 A | 4/1998 | Umber et al. | |
| 5,928,241 A | 7/1999 | Menut et al. | |
| 6,179,302 B1 | 1/2001 | Gauthier et al. | |
| 6,722,667 B2 * | 4/2004 | Cantlon | 279/22 |
| 7,086,313 B2 | 8/2006 | Cantlon | |
| 7,810,817 B1 | 10/2010 | Gao | |

\* cited by examiner

*Primary Examiner* — Kevin T Truong
*Assistant Examiner* — Si Ming Lee
(74) *Attorney, Agent, or Firm* — Absolute Technology Law Group

(57) ABSTRACT

The present invention is a self-locking internal adapter for D-shaped orthopedic tools. A locking ball mechanism prevents movement of the adapter components relative to each other, while a plurality of securing ball mechanisms releasably secure a D-shaped orthopedic tool in the adapter. A chamfered surface of the adapter engages a chamfer of the tool to centrally stabilize the tool in the adapter. The internal adapter may be used with driver handles, ratcheting handles and torque-limiting handles.

20 Claims, 11 Drawing Sheets

SELF-LOCKING INTERNAL ADAPTER FOR D-SHAPED ORTHOPEDIC ADJUSTMENT TOOLS

FIELD OF INVENTION

The present invention relates to the field of medical devices, and more specifically to a self-locking internal adapter for securing medical tools.

TERMS OF ART

Figure 1:
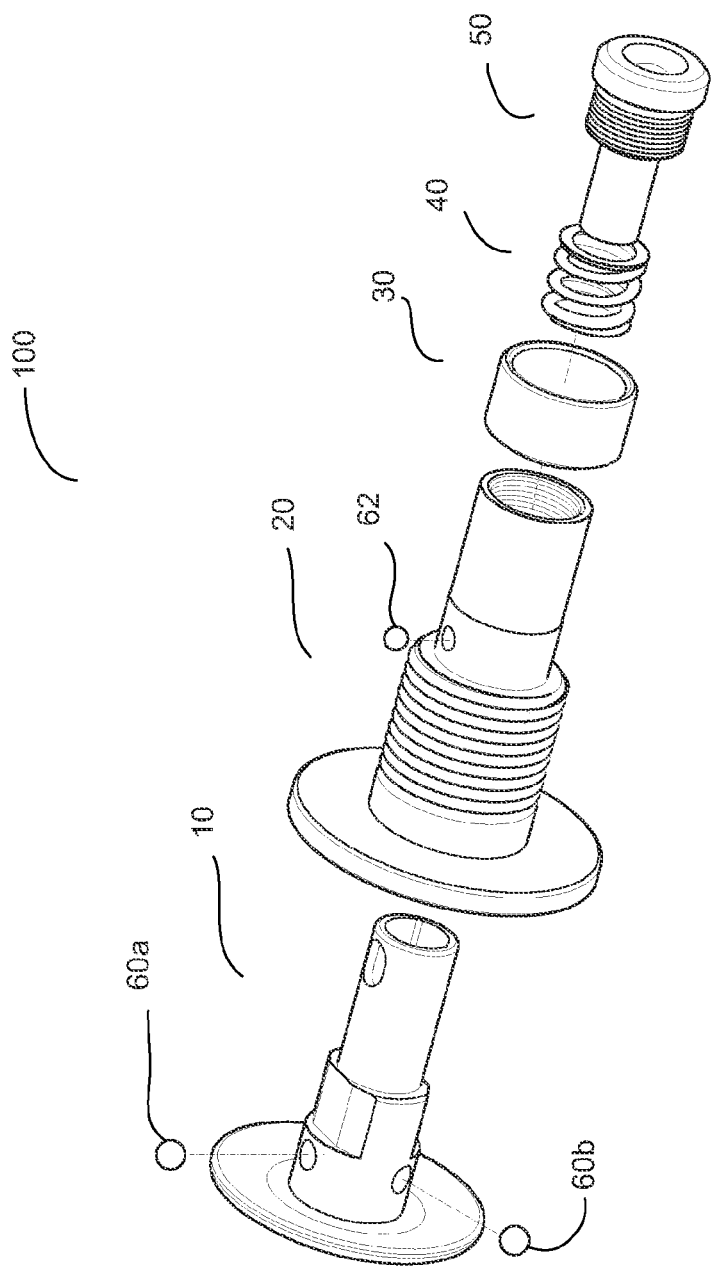
FIG. 1 is an exploded view of an exemplary embodiment of an internal adapter for a medical handle.

As used herein, the term "adapter" refers to a component of an orthopedic tool handle which engages a tool.

As used herein, the term "chamfer" refers to a beveled, angled or tapered edge which engages the edge of a second component to create a secured junction.

As used herein, the term "D-shaped" refers to a substantially cylindrical shape with a single flattened or partially flattened portion.

As used herein, the term "D-shaped shaft" refers to a shaft having a single flattened or partially flattened portion.

As used herein, the term "D-shaped tool stem" refers to a tool stem having a single flattened or partially flattened portion.

As used herein, the terms "flattened portion" or "partially flattened portion" refer to a cylindrical surface having an area with a curvature less than that of the cylindrical curvature. A flattened or partially flattened portion may contain a single area or multiple areas of lesser curvature.

BACKGROUND

Adjustment tools are used in orthopedic surgery to tighten and adjust mechanical components within orthopedic devices. For example, screwdrivers, spreaders, pliers, hammers, cutters and other tools may be used to adjust screws, pins, rods and other orthopedic devices. The adjustment tools for adjusting these orthopedic devices must be highly stable to allow for precise adjustments, and many types of adjustments may be needed.

In order to save space on an operating room instrument table or in a sterilization kit, different orthopedic tools may be designed to be interchangeable with a single handle. For example, it is known in the art to fashion tools of varying lengths with shafts that may be inserted into a single tool handle.

As a result, a typical orthopedic tool may actually be a system of three components: a handle, an adapter and a tool. Generally, the handle and the adapter are structurally integrated and permanently attached to each other. Tools are adapted for insertion into the adapter.

Adapters for securing medical tools to handles are known in the art.

For example, U.S. Pat. No. 7,810,817 discloses an adapter for securing medical tools to drivers.

The AO Foundation has established orthopedic standards in the medical field, including standard instrumentation specification. Tools having a D-shaped shaft are known in the art and part of the AO Foundation's standard instrumentation. Tools with a D-shaped shaft may be attached to a variety of handles, depending on how the tool is to be used, but the tools require a specific adapter having a corresponding D-shaped aperture. These assemblies are known in the art, and the D-shaped configuration prevents rotation during a surgical procedure.

Every adapter has some sort of channel or orifice to receive the tool, and a locking mechanism to secure the tool in place. The function and simplicity of operating the locking mechanism are critical. Even incremental improvements in a locking mechanism can be critical to the outcome of a surgery.

Tools must be compact to allow an orthopedic surgeon to perform adjustments to orthopedic devices and other tasks within the confined space of various body regions.

Tools must also be versatile, and it is desirable to have as many tools as possible adapted for use with a single adapter and handle.

Adapter components are likely to come in contact with bodily fluids and other contaminants during medical procedures. Any contours, grooves and other hard-to-reach surfaces need to be carefully cleaned and sterilized. Exposed attachment components are also more likely to be bumped or inappropriately forced in an attempt to attach a medical tool. As a result, exposed attachment components are frequently damaged.

It is desirable to have an adapter for securing medical tools to handles which reduce the number of exposed components and surfaces.

It is desirable to have an apparatus for securing and grasping tools which is as compact as possible so that surgeons can operate within the limited spaces and contours of various regions of the body.

It is critical to have an adapter for securing medical tools in place as effectively and simply as possible.

SUMMARY OF THE INVENTION

The present invention is an internal adapter for use in handles for D-shaped orthopedic tools. A locking ball mechanism slidingly secures a collar assembly within an interior collar channel of a driver assembly. The collar assembly, having an internal D-shaped tool receiving channel, contains a plurality of securing ball mechanisms which decrease the interior diameter of the internal D-shaped tool receiving channel. The driver assembly has a tapered interior surface, creating an area of smaller diameter near the front of the interior collar channel and an area of larger diameter near the rear of the interior collar channel.

A spring provides outward force on the collar assembly, which is prevented from extending outward from the handle by the locking ball mechanism. When a D-shaped tool is inserted into the internal D-shaped tool receiving channel, the securing ball mechanisms prevent outward movement of the tool. Providing an inward force on the collar assembly to compress the spring moves the securing ball mechanisms to an area of the interior collar channel having a larger diameter, thereby increasing the diameter of the internal D-shaped tool receiving channel to release the tool.

DETAILED DESCRIPTION OF INVENTION

For the purpose of promoting an understanding of the present invention, references are made in the text to exemplary embodiments of a self-locking internal adapter, only some of which are described herein. It should be understood that no limitations on the scope of the invention are intended by describing these exemplary embodiments. One of ordinary skill in the art will readily appreciate that alternate but functionally equivalent structures and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

FIG. 1 is an exploded view of an exemplary embodiment of internal adapter 100 for an orthopedic tool handle specifically adapted to receive D-shaped tool shafts. In the exemplary embodiment shown, internal adapter 100 has five internal base components: quick-release collar assembly 10, driver assembly 20, sleeve 30, spring 40 and internal shaft stop assembly 50. Also shown in FIG. 1 are securing balls 60a, 60b, 60c (not shown) and locking ball 62.

In the exemplary embodiment illustrated in FIG. 1, quick-release collar assembly 10, driver assembly 20, sleeve 30, spring 40 and internal shaft stop assembly 50 are each separate, integrally machined components. In further exemplary embodiments, quick-release collar assembly 10, driver assembly 20, sleeve 30, spring 40 and internal shaft stop assembly 50 may be made of multiple sub-components. In still further exemplary embodiments, two or more components may be integrally machined as a single component.

Figure 2A:
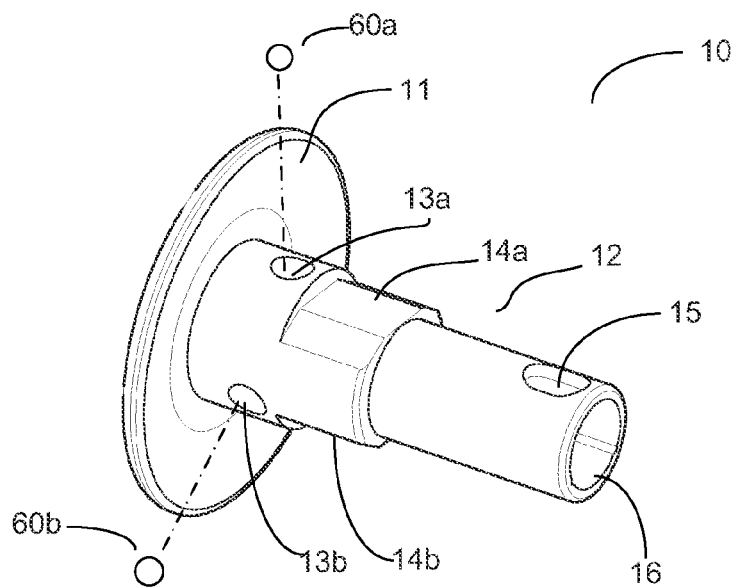
FIGS. 2a and 2b illustrate an exemplary embodiment of a collar assembly for an internal adapter.
Figure 2B:
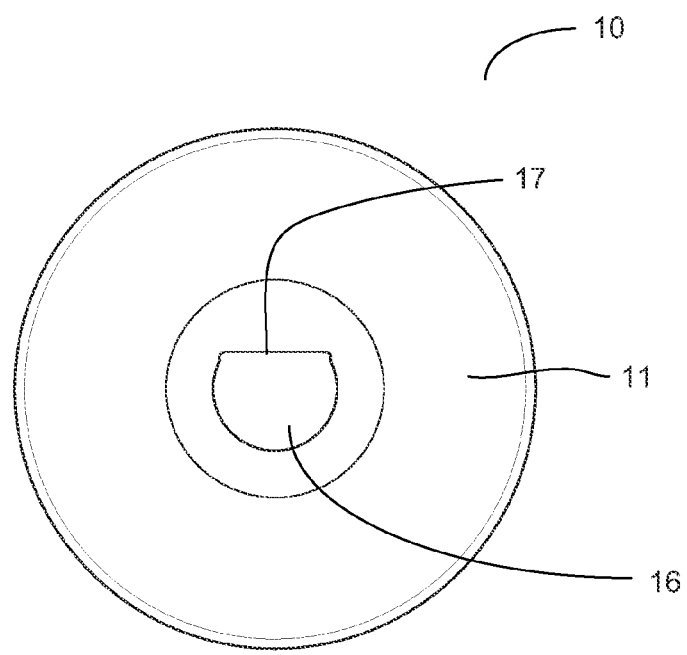

FIGS. 2a and 2b illustrate exemplary embodiments of quick-release collar assembly 10 for internal adapter 100.

Quick-release collar assembly 10 has external collar base 11 and internal tubular sliding portion 12. External collar base 11 may protrude from a handle when internal adapter 100 is assembled. As illustrated in the exemplary embodiments shown in FIGS. 2a and 2b, external collar base 11 and internal tubular sliding portion 12 are a single machined component. In further exemplary embodiments, external collar base 11 and internal tubular sliding portion 12 may be separately manufactured and later assembled.

In the exemplary embodiment shown, internal tubular sliding portion 12 has three securing ball engaging apertures 13a, 13b, 13c (not shown) evenly spaced and symmetrically arranged around internal tubular sliding portion 12 and corresponding to securing balls 60a, 60b, 60c (not shown). In further exemplary embodiments, quick-release collar assembly 10 may have more securing ball engaging apertures symmetrically arranged around internal tubular sliding portion 12. While in some exemplary embodiments asymmetrically arranged securing ball engaging apertures 13a, 13b, 13c and securing balls 60a, 60b, 60c may be used, symmetrically arranging securing ball engaging apertures 13a, 13b, 13c and securing balls 60a, 60b, 60c provides even securing force for securing a D-shaped orthopedic tool.

Securing ball engaging apertures 13a, 13b, 13c (not shown) are contoured on their inward facing edge to have a diameter smaller than the diameter of corresponding securing balls 60a, 60b, 60c (not shown) to prevent securing balls 60a, 60b, 60c (not shown) from falling through securing ball engaging apertures 13a, 13b, 13c (not shown) while allowing securing balls 60a, 60b, 60c (not shown) to remain freely rotatable within securing ball engaging apertures 13a, 13b, 13c (not shown). In further exemplary embodiments, securing ball engaging apertures 13a, 13b, 13c (not shown) may contain a lip, ridge, protuberance, cushion, rim or other structure, device or combination of structures and devices to narrow the diameter of the inward facing edge of securing ball engaging apertures 13a, 13b, 13c (not shown).

Figure 5:
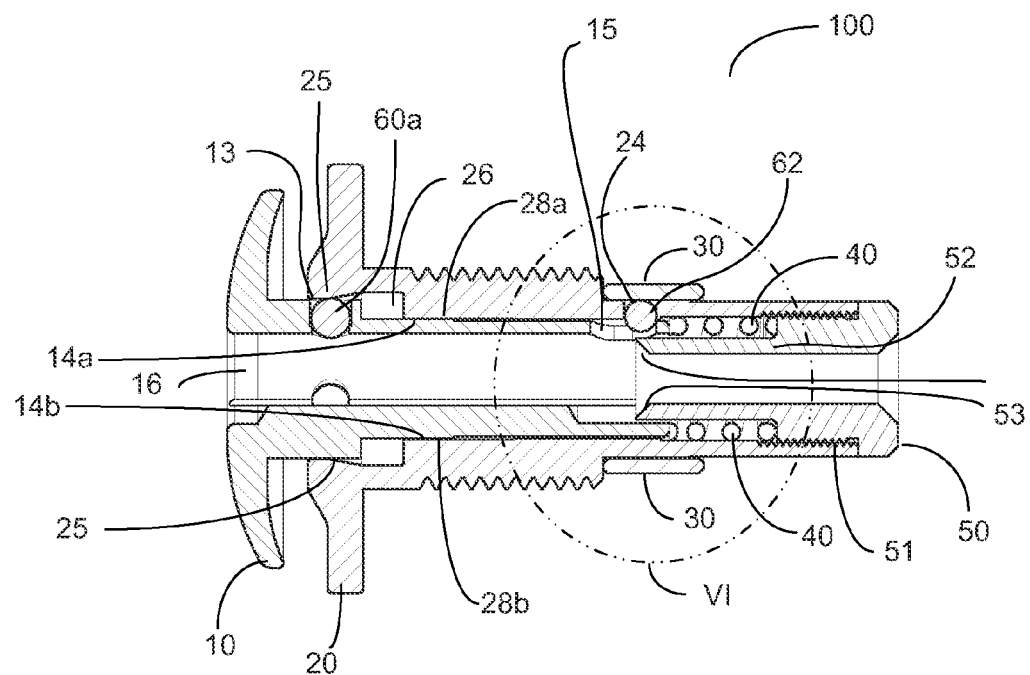
FIG. 5 is a cross-sectional view of an exemplary embodiment of an assembled internal adapter.

As illustrated in FIG. 2a, internal tubular sliding portion 12 also has two flattened portions 14a, 14b situated on opposite sides of internal tubular sliding portion 12. The remainder of internal tubular sliding portion 12 is cylindrical with locking ball slot 15. Flattened portions 14a, 14b correspond to flattened portions 28a, 28b (not shown) of driver assembly 20 (not shown) to rotationally secure collar assembly 10 within interior collar channel 26, as illustrated in FIG. 5.

In the exemplary embodiment illustrated in FIG. 2a, flattened portions 14a, 14b consist of three adjacent flattened surfaces, each angled relative to the curvature of internal tubular sliding portion 12. In further exemplary embodiments, flattened portions 14a, 14b may consist of a single flattened or partially flattened surface. In still further exemplary embodiments, internal tubular sliding portion 12 may contain a single flattened portion or more flattened portions symmetrically or asymmetrically arranged around internal tubular sliding portion 12.

Internal D-shaped tool receiving channel 16 extends the length of quick-release collar assembly 10. As shown in FIG. 2b, internal D-shaped tool receiving channel 16 is a substantially cylindrical channel having flattened portion 17 to create a D-shape. While in the exemplary embodiment shown, internal D-shaped tool receiving channel 16 is D-shaped for its entire length, in further exemplary embodiments, internal D-shaped tool receiving channel 16 may be D-shaped only for a portion of its length.

Figure 3A:
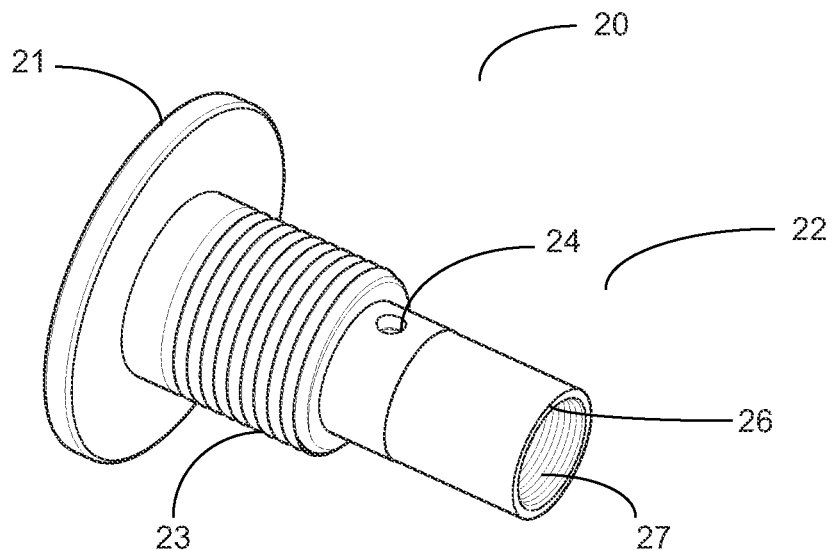
FIGS. 3a, 3b and 3c illustrate an exemplary embodiment of a driver assembly for an internal adapter.
Figure 3B:
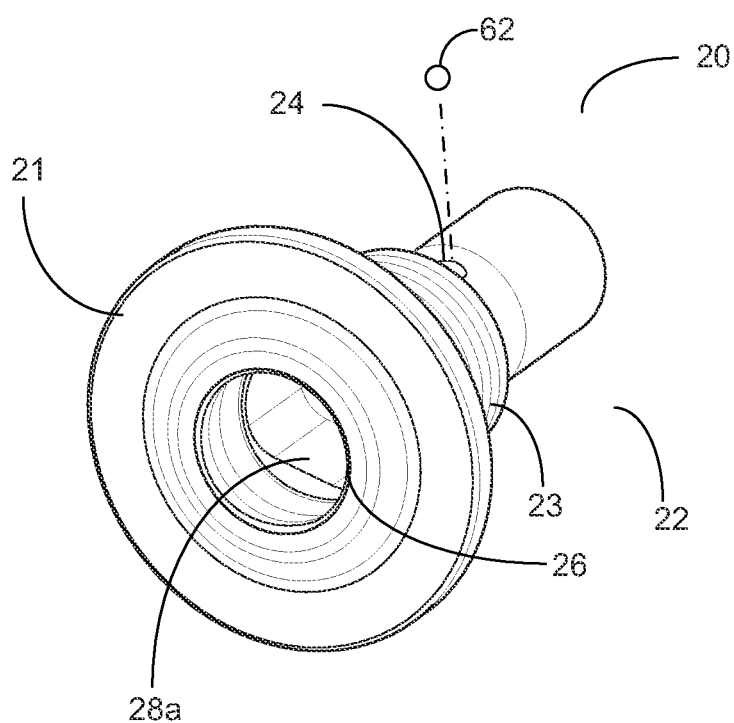
Figure 3C:
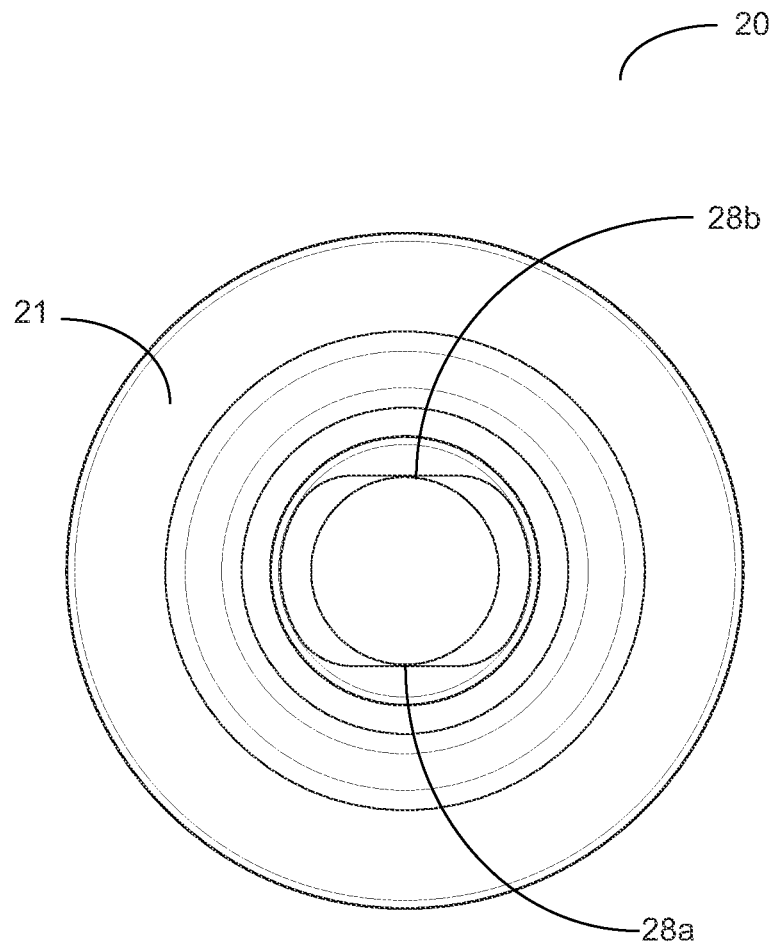

FIGS. 3a, 3b and 3c illustrate an exemplary embodiment of driver assembly 20 for internal adapter 100.

As illustrated in FIGS. 3a and 3b, driver assembly 20 has external driver base 21 and interior handle-connecting portion 22. External driver base 21, along with external collar base 11, may protrude from a handle when internal adapter 100 is assembled.

Interior handle-connecting portion 22 has threaded handle engaging portion 23. As will be illustrated in FIG. 7, when assembled, internal adapter 100 engages a handle which has an internal handle cavity with threads corresponding to threaded handle engaging portion 23. In further exemplary embodiments, interior handle-connecting portion 22 may be adapted to secure to an internal handle cavity with any other structure or device known in the art, including, but not limited to, adhesives, pins, locking mechanisms, brackets, screws, contours, friction-fit components, and combination of these structures and devices. In still further exemplary embodiments, driver assembly 20 may be an integral component of a handle.

The remainder of interior handle-connecting portion 22 is cylindrical with locking ball aperture 24. Locking ball aperture 24 is contoured on its inward facing edge to have a diameter smaller than locking ball 62 to prevent locking ball 62 from falling through locking ball aperture 24 while allowing locking ball 24 to freely rotate. In further exemplary embodiments, locking ball aperture 24 may contain any other structure, device, or combination of structures and devices which create a smaller diameter along the inward facing edge of locking ball aperture 24, including, but not limited to, a lip, ridge, protuberance, cushion, rim or combination thereof.

Interior collar channel 26 extends the length of driver assembly 20 with rear threaded portion 27. As shown in FIGS. 3b and 3c, interior collar channel 26 contains a two flattened portions 28a, 28b which correspond to flattened portions 14a, 14b (not shown) of collar assembly 10. Flattened portions 28a, 28b of driver assembly 20 and flattened portions 14a, 14b (not shown) of collar assembly 10 prevent rotational movement of collar assembly 10 within interior collar channel 26 when internal adapter 100 is assembled.

As illustrated in FIGS. 3b and 3c, flattened portions 28a, 28b each consist of three flattened surfaces, each angled relative to the curvature of internal tubular sliding portion 12 (not shown) of collar assembly 10 (not shown) to correspond to the three flattened surfaces of flattened portions 14a, 14b (not shown). In further exemplary embodiments, flattened portions 28a, 28b may be any number of flattened surfaces in order to correspond to flattened portions 14a, 14b (not shown). In further exemplary embodiments, interior collar channel 26 may have more or fewer flattened portions to match collar assembly 10.

Figure 4:
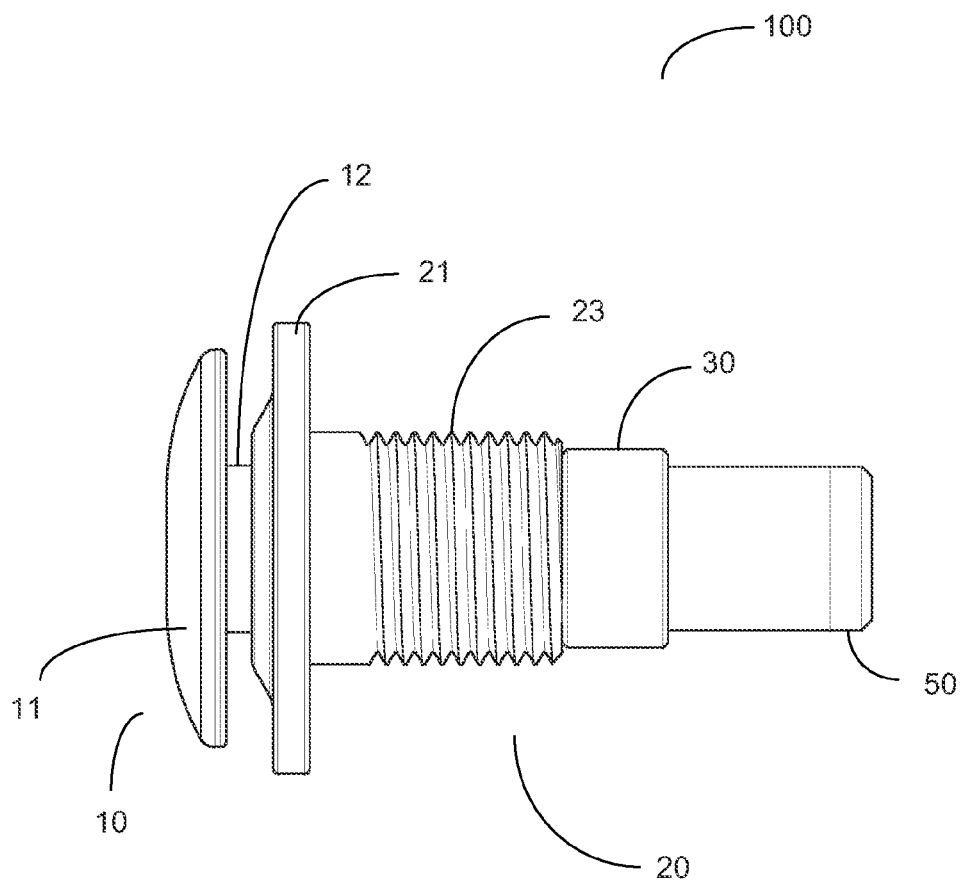
FIG. 4 is an exemplary embodiment of an assembled internal adapter.

FIG. 4 illustrates an external view of assembled internal adapter 100. Collar assembly 10 is slidingly engaged with driver assembly 20, with spring 40 (not shown) contained inside driver assembly 20 by internal shaft stop assembly 50. Sleeve 30 is secured over driver assembly 20.

As illustrated in FIG. 4, spring 40 (not shown) provides an outward force on collar assembly 10, which is held a distance away from driver assembly 20, exposing a portion of internal tubular sliding portion 12. Inward pressure may be exerted on exterior collar base 11 to compress spring 40 (not shown) and push collar assembly 10 inward in internal adapter 100.

FIG. 5 is a cross-sectional view of an exemplary embodiment of an assembled internal adapter 100.

As illustrated in FIG. 5, the internal diameter of interior collar channel 26 is larger than the exterior diameter of internal tubular sliding portion 12, allowing interior collar channel 26 to slidingly receive internal tubular sliding portion 12 such that collar assembly 10 has limited free sliding movement within interior collar channel 26. Flattened surfaces 28a, 28b and flattened portions 14a, 14b align to prevent rotational movement of collar assembly 10 within interior collar channel 26.

In the exemplary embodiment shown, when collar assembly 10 and driver assembly 20 are assembled, locking ball slot 15 aligns with locking ball aperture 24. Locking ball 62 remains in freely rotatable position in locking ball aperture 24 and engages locking ball slot 15 to limit the sliding movement of collar assembly 10 within interior collar channel 26. In further exemplary embodiments, any locking system, structure or device known in the art may be used to limit the sliding movement of collar assembly 10 within interior collar channel 26, including, but not limited to, pins, pressure force, spring assemblies, and any combination of locking systems, structures or devices.

Sleeve 30 has a smooth, cylindrical outer surface and smooth, cylindrical inner surface, with an inner diameter greater than the outer diameter of the unthreaded portion of handle-connecting portion 22 of driver assembly 20. Sleeve 30 sits over locking ball aperture 24 of driver assembly 20 to prevent locking ball 62 from disengaging locking ball aperture 24.

Spring 40 has an outer coil diameter less than the inner diameter of interior collar channel 26. When internal adapter 100 is assembled, spring 40 provides force on collar assembly 10, keeping it at an outward position.

As illustrated in FIG. 5, driver assembly 20 provides an outer surface over securing balls 60a (60b, 60c not shown) to prevent securing balls 60a (60b, 60c not shown) from disengaging securing ball apertures 13a (13b, 13c not shown).

The interior surface of interior collar channel 26 which covers securing balls 60a (60b, 60c not shown) is angled at tapered surface 25. Near the front of interior collar channel 26, tapered surface 25 decreases the internal diameter of interior collar channel 26, creating a region of smaller volume for securing ball apertures 13a (13b, 13c not shown). As tapered surface 25 angles outward, the volume of securing ball apertures 13a (13b, 13c not shown) increases.

Tapered surface 25 allows securing balls 60a (60b, 60c not shown) to securely engage an orthopedic tool. When a tool is inserted in internal D-shaped tool receiving channel 16, the surface of securing balls 60a (60b, 60c not shown) engages the surface of the tool. When the tool is pushed forward, or into internal adapter 100, securing balls 60a (60b, 60c not shown), freely rotate along the surface of the tool, allowing the tool to slide into internal adapter 100. Securing balls 60a (60b, 60c not shown) freely rotate because tapered surface 25 provides rotational space.

If the orthopedic tools is pulled back, or out of internal adapter 100, securing balls 60a (60b, 60c not shown) are unable to rotate along the tool surface. Spring 40 keeps outward pressure on collar assembly 10, preventing collar assembly 10 from moving further into driver assembly 20 and increasing the size of securing ball apertures 13a, 13b, 13c.

To release an orthopedic tool, collar assembly 10 is pressed inward to compress spring 40, allowing securing balls 60a (60b, 60c not shown) to freely rotate in securing ball apertures 13a (13b, 13c not shown). When collar assembly 10 is forced inward, securing ball apertures 13a (13b, 13c not shown) increase in size because of tapered surface 25 of interior collar channel 26.

Internal shaft stop assembly 50 has threaded portion 51 and shaft stop portion 52. Shaft stop portion 52 has an outer diameter less than the inner coil diameter of spring 40, so that spring is secured around shaft stop portion 52. Threads of threaded portion 51 correspond to rear threaded portion 27 of driver assembly 20 to secure internal shaft stop assembly 50 when internal adapter 100 is assembled. Shaft stop portion 52 also contains chamfer 53.

Figure 6:
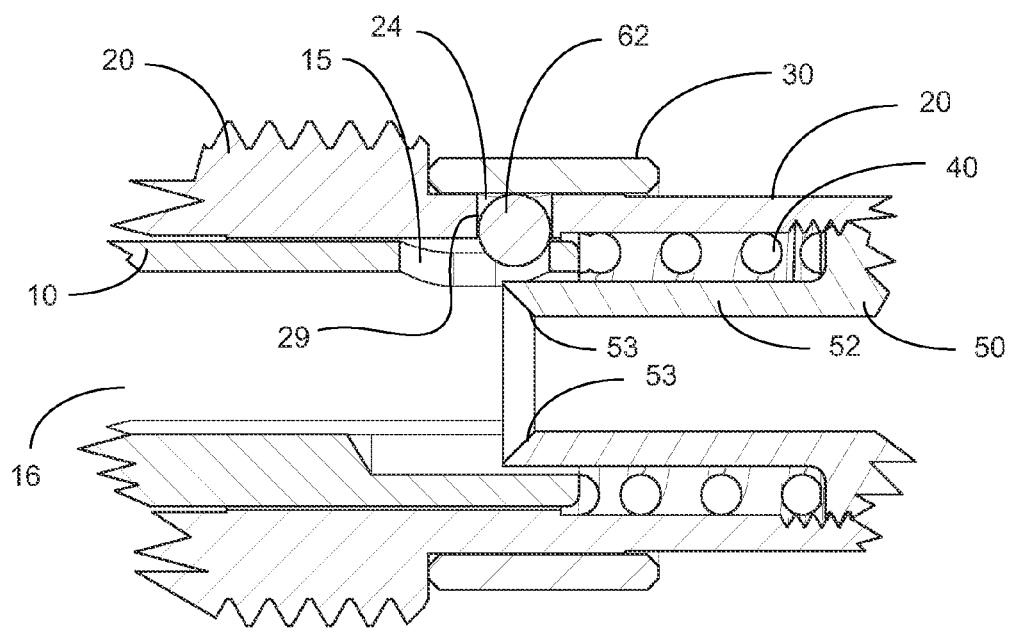
FIG. 6 is an exemplary embodiment of an internal adapter locking mechanism.

FIG. 6 illustrates an exemplary embodiment of an internal adapter 100 self-locking mechanism. When internal adapter 100 is assembled, locking ball 62 secured in locking ball aperture 24 of driver assembly aligns with locking ball slot 15 of collar assembly. Sleeve 30 covers locking ball aperture 24 to prevent locking ball 62 from disengaging locking ball aperture 24.

Locking ball aperture 24 has contoured surface 29. Contoured surface 29 gives locking ball aperture 24 a diameter less than the greatest diameter of locking ball 62 at the inner-most point of locking ball aperture 24. The diameter of the remainder of locking ball aperture 24 is greater than that of locking ball 62.

In the exemplary embodiment shown, locking ball slot 15 has a length approximately equal to the length of tapered surface 28 (not shown) and a width approximately equal to the diameter of locking ball 62 which engages locking ball slot 15.

As illustrated in FIG. 6, spring 40 provides force on collar assembly 10 to keep collar assembly 10 in an outward position. While collar assembly 10 is in a forced outward position, locking ball 62 engages the inner-most surface locking ball slot 15 and prevents spring 40 from forcing collar assembly 10 out of driver assembly 20.

When collar assembly 10 is pushed inward and spring 40 compressed, locking ball slot 15 is also forced inward so that locking ball 62 engages the outer-most surface of locking ball slot 15. Collar assembly 10 is therefore prevented from being pushed too far into driver assembly 20.

Locking ball 62 and locking ball slot 15, along with flattened surfaces 28a, 28b of driver assembly 20 and flattened portions 14a, 14b of collar assembly 10, help prevent rotational movement of collar assembly 10 within interior collar channel 26 when internal adapter 100 is assembled. Locking ball 62, locking ball slot 15 and locking ball aperture 24 also function together to secure collar assembly 10 within driver assembly 20.

Figure 7:
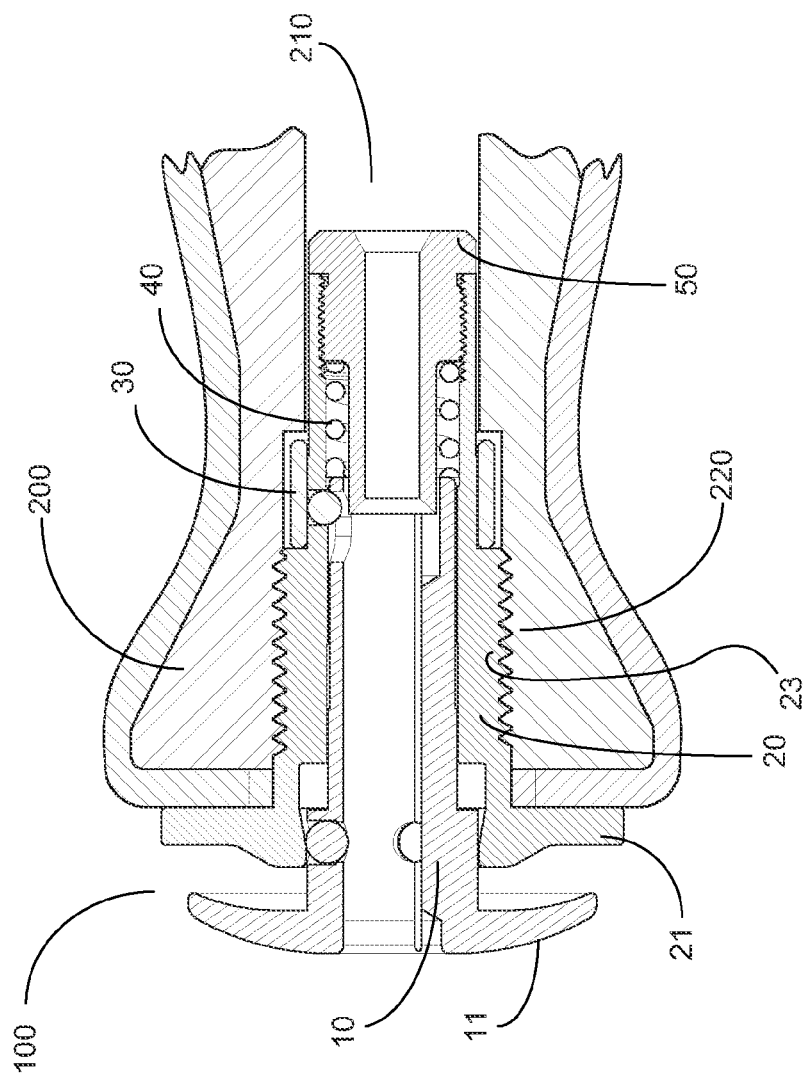
FIG. 7 is an exemplary embodiment of an internal adapter secured to a handle.

FIG. 7 is an exemplary embodiment of internal adapter 100 secured in handle 200. In the exemplary embodiment shown, handle 200 has internal cavity 210 with threaded portion 220. Internal adapter 100 is secured in internal cavity 210 by threaded handle engaging portion 23. Threads of threaded handle engaging portion 23 correspond to and engage threads of internal cavity threaded portion 220.

Figure 8:
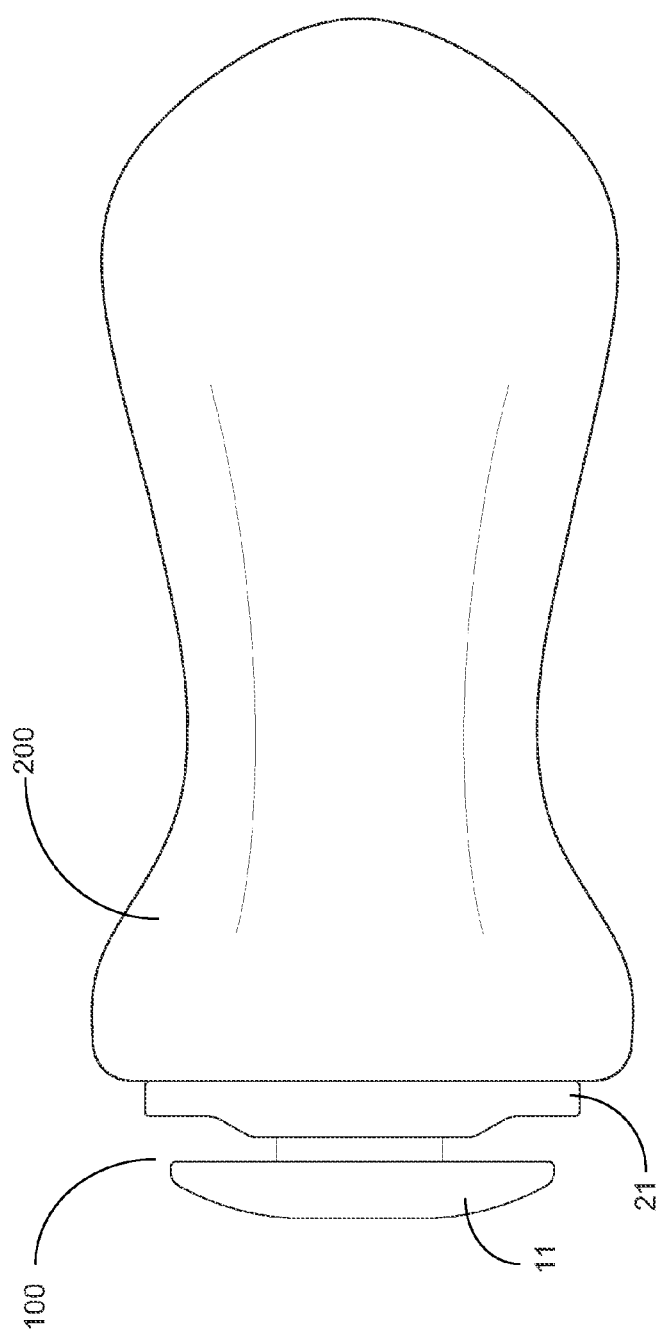
FIG. 8 illustrates exterior components of an internal adapter secured to a handle.

As further illustrated in FIG. 8, the only portions of internal adapter 100 exposed outside handle are collar base portion 11 and driver base portion 21.

As illustrated in the exemplary embodiments shown in FIGS. 7 and 8, internal adapter 100 is used with a drive handle. In further exemplary embodiments, internal adapter 100 may be used with many style handles, including, but not limited to, torque-limiting handles and ratcheting handles.

Figure 9:
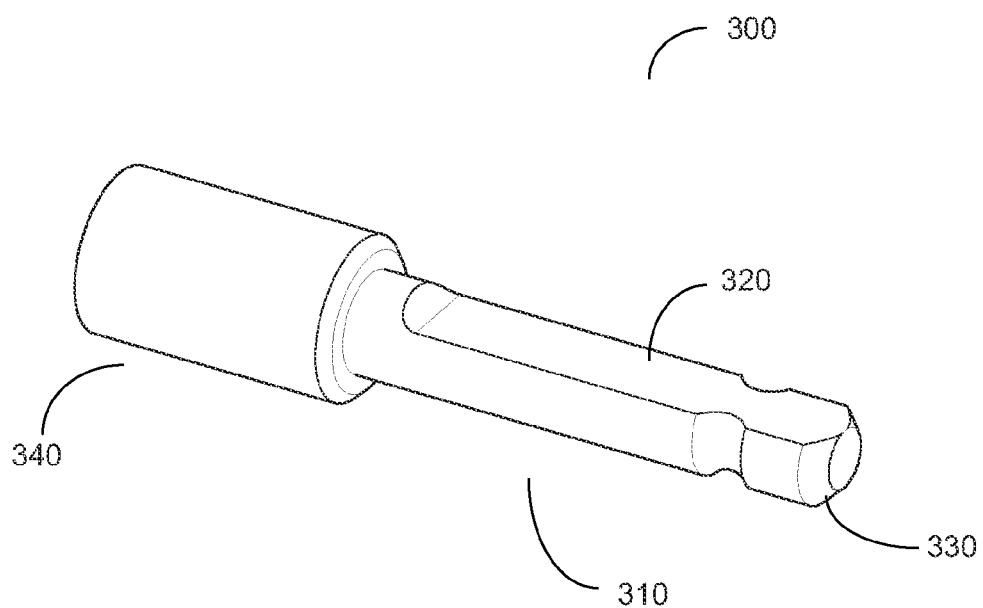
FIG. 9 is an exemplary embodiment of a D-shaped orthopedic tool for use with an internal adapter.

FIG. 9 is an exemplary embodiment of D-shaped orthopedic tool 300 for use with internal adapter 100 (not shown). Tool 300 has D-shaped shaft 310 with flattened surface 320 and chamfer 330. Chamfer 330 surrounds the entire end of shaft 310 except where flattened surface 320 intersects.

In the exemplary embodiment shown, tool extension 340 is a cylindrical rod. In further exemplary embodiments, tool extension 340 may contain any type of orthopedic tool known in the art. Tool extension 340 may also be longer or shorter in order to provide a tool with the length necessary to allow a surgeon to reach a specific body location.

Figure 10:
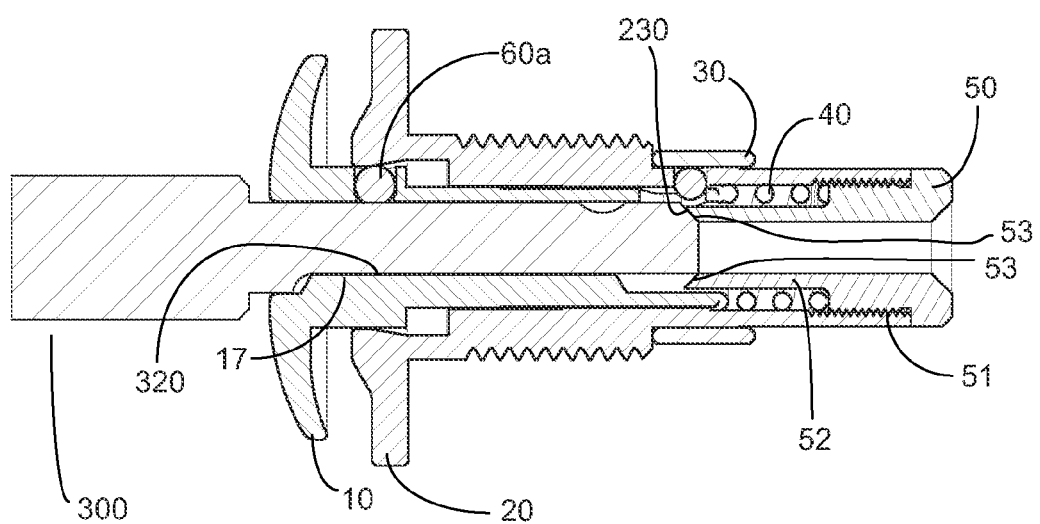
FIG. 10 is a cross-sectional view of a D-shaped orthopedic tool in use with an exemplary internal adapter.

FIG. 10 is a cross sectional view of an exemplary embodiment of internal adapter 100 in use with D-shaped orthopedic tool 300. D-shaped orthopedic tool 300 is secured in internal D-shaped tool receiving channel 16, with flattened surface 320 oriented downward to match flattened portion 17.

As illustrated in FIG. 10, stop shaft portion 52 of internal shaft stop assembly 50 has chamfer 53 which corresponds to chamfer 330 of tool 300. As illustrated, when tool 300 is completely inserted in internal D-shaped tool receiving channel 16, chamfer 330 engages chamber 53 and secures and stabilizes D-shaped orthopedic tool 300 in a central position within internal D-shaped tool receiving channel 16.

Securing balls 60a, 60b, 60c (not shown) engage D-shaped shaft 310 and prevent outward movement of shaft 310 in internal D-shaped tool receiving channel 16. As tool 300 is pushed into internal D-shaped tool receiving channel 16, securing balls 60a, 60b, 60c (not shown) are pushed within securing ball engaging apertures 13a, 13b, 13c (not shown) towards the region of larger volume created by tapered surface 25, allowing securing balls 60a, 60b, 60c (not shown) to freely rotate along shaft 310. If tool 300 is pulled outward from internal D-shaped tool receiving channel 16, securing balls 60a, 60b, 60c (not shown) are pulled in securing ball engaging apertures 13a, 13b, 13c towards the region of smaller volume, and securing balls 60a, 60b, 60c are in a position unable to rotate. As a result, securing balls 60a, 60b, 60c (not shown) are unable to rotatably engage shaft 310, and shaft 310 is locked in internal D-shaped tool receiving channel 16.

To release tool 300, exterior collar base 11 may be pushed inward, compressing spring 40 and moving collar assembly 10 inward in interior collar channel 26. Securing balls 60a, 60b, 60c (not shown) are therefore forced to the region of larger volume, allowing securing balls 60a, 60b, 60c (not shown) space to freely rotate along shaft 310 as shaft 310 is pulled out of internal D-shaped tool receiving channel 16.

Figure 11:
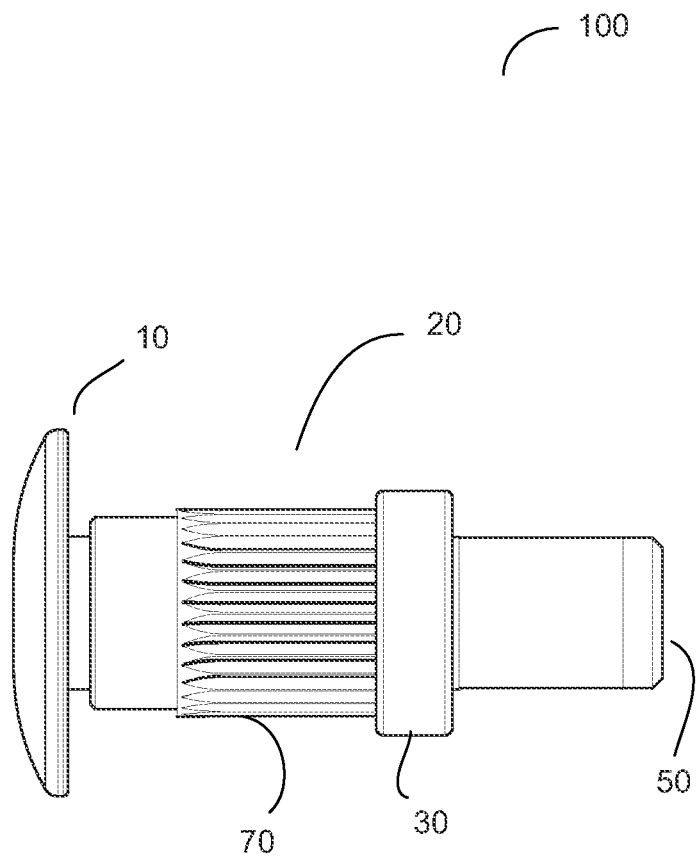
FIG. 11 is an exemplary embodiment of an internal adapter for use with a ratcheting mechanism.

FIG. 11 is an alternative embodiment of internal adapter 100 for use with a handle containing a ratcheting mechanism. In the exemplary embodiment shown, driver assembly 20 does not contain threaded handle engaging portion 23. Rather, driver assembly contains gear teeth 70.

Figure 12:
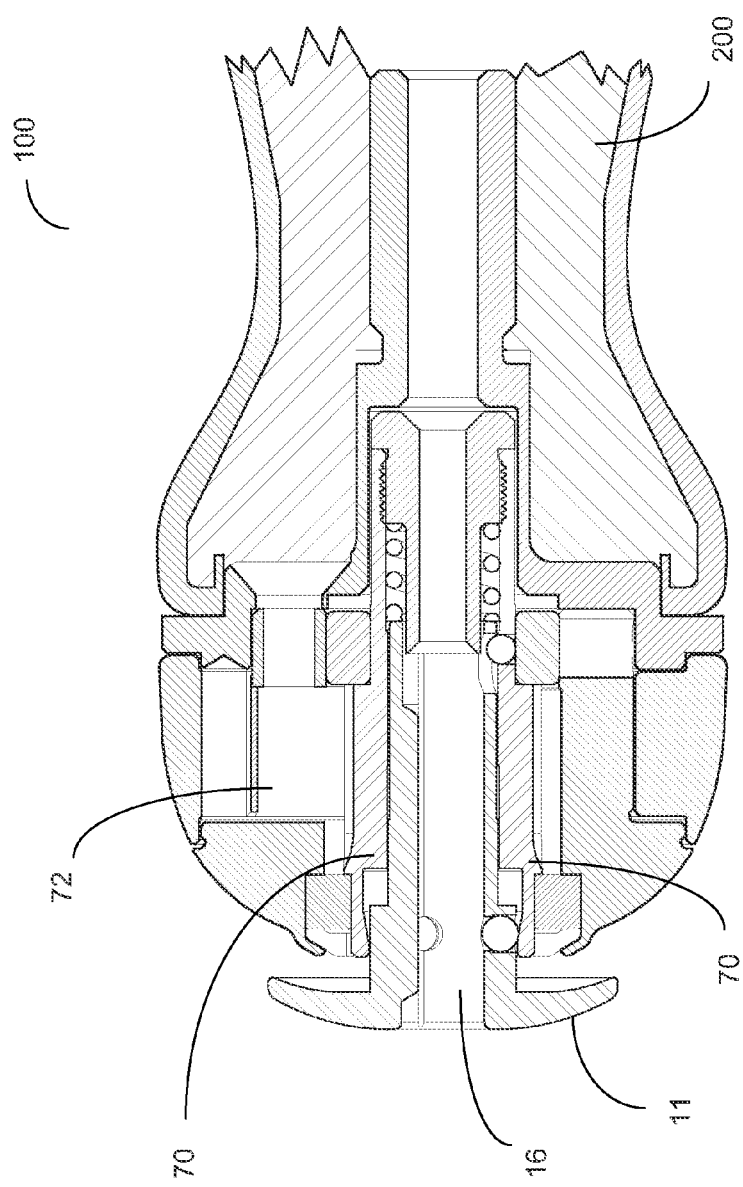
FIG. 12 is an exemplary embodiment of an internal adapter for use with a ratcheting mechanism in use with a ratcheting handle.

As illustrated in FIG. 12, gear teeth 70 engage ratcheting drive mechanism 72 in handle 200. Driver assembly 20 does not contain external driver base, and only external collar base 11 protrudes from handle 200.

What is claimed is:

1. An orthopedic tool apparatus for D-shaped tool shafts with a chamfer end comprised of:
at least one housing forming a handle and having an internal cavity; and
at least one internal D-shaped tool adapter comprised of
a slidable collar assembly with an internal D-shaped tool receiving channel, said collar assembly having a plurality of equidistant securing ball apertures and at least one locking ball slot,
a driver assembly with an interior collar channel having a tapered surface creating a smaller interior collar channel diameter at a front of said interior collar channel and a larger interior collar channel diameter at a rear end of said interior collar channel and at least one locking ball aperture corresponding to said at least one locking ball slot, wherein said slidable collar assembly is slidable within said interior collar channel and said plurality of securing ball apertures are aligned with said tapered surface,
a plurality of securing balls wherein each one of said plurality of securing balls engages one of said plurality of securing ball apertures to decrease a diameter of said D-shaped tool receiving channel,
at least one locking ball engaging said at least one locking ball aperture and said at least one locking ball slot,
a spring adapted to provide outward force on said slidable collar assembly so that said plurality of securing balls are aligned with said smaller interior collar channel diameter and said locking ball engages an inner-most surface of said locking ball slot to prevent outward movement of said slidable collar assembly, and
a shaft stop assembly having a chamfer corresponding to said chamfer of said D-shaped tool;

wherein inward force applied to said slidable collar assembly aligns said plurality of securing balls with said larger interior collar channel diameter to increase a diameter of said D-shaped tool receiving channel and said locking ball engages an outer-most surface of said locking ball slot to prevent further inward movement of said slidable collar assembly.

2. The apparatus of claim 1 wherein said internal handle cavity and said driver assembly have corresponding threads.

3. The apparatus of claim 1 wherein said driver assembly has gear teeth for use with a ratcheting handle.

4. The apparatus of claim 1 which has three securing balls and securing ball apertures.

5. The apparatus of claim 1 which further includes a sleeve adapted to secure said locking ball in said locking ball aperture.

6. The apparatus of claim 1 wherein an exterior surface of said collar assembly has at least one flattened portion.

7. The apparatus of claim 6 wherein an interior surface of said interior collar channel has at least one flattened surface corresponding to said at least one flattened portion of said collar assembly to prevent rotational movement of said collar assembly within said interior collar channel.

8. The apparatus of claim 1 wherein said at least one locking ball is freely rotatable in said locking ball aperture and said plurality of securing balls are freely rotatable in said securing ball apertures.

9. The apparatus of claim 1 wherein said collar assembly includes an external collar base.

10. A handle for a medical shaft comprised of:
an integrally machined collar assembly having a collar base portion, an internal D-shaped tool receiving channel and an internal tubular sliding portion, wherein said internal tubular sliding portion contains three securing ball apertures symmetrically arranged around said tubular sliding portion and a locking ball slot;
an integrally machined driver assembly comprised of a driver base portion, an interior collar channel and a cylindrical interior handle-connecting portion having a locking ball aperture corresponding to said locking ball slot, wherein said interior collar channel has a tapered portion of interior surface near a front of said interior collar channel;
wherein said internal tubular sliding portion of said collar assembly is slidingly engaged with said interior collar channel of said driver assembly such that said three securing ball apertures are aligned with said tapered portion of said interior collar channel;
three securing balls, each engaged with and freely rotatable in one of said securing ball apertures, wherein said tapered portion of said interior collar engaging channel secures said securing balls in said securing ball apertures;
a locking ball engaged with and freely rotatable in said locking ball aperture and said locking ball slot, wherein said locking ball is secured in said locking ball aperture by a sleeve;
a spring having an outer diameter which is smaller than a diameter of said interior collar channel allowing said spring to be inserted in said interior collar channel to provide an outward force on said collar assembly, wherein outward movement of said collar assembly is prevented by said locking ball engaging said locking ball slot; and
a shaft stop assembly securing said spring within said interior collar channel, wherein said shaft stop assembly has a chamfer corresponding to the chamfer of a D-shaped orthopedic tool;
wherein said collar assembly, said driver assembly, said securing balls, said locking ball, said spring and said shaft stop are internally housed within a medical tool handle.

11. The apparatus of claim 10 wherein said driver assembly further includes a partially threaded outer surface.

12. The apparatus of claim 10 wherein said medical tool handle is selected from the group consisting of a drive handle, a ratcheting handle and a torque-limiting handle.

13. The apparatus of claim 10 wherein said securing ball apertures and said locking ball aperture are contoured on their inward facing edge to have a diameter smaller than a diameter of said securing balls and said locking ball.

14. The apparatus of claim 10 wherein said collar base portion and said driver base portion are external to said handle.

15. The apparatus of claim 10 wherein said internal tubular sliding portion and said interior collar channel have at least two corresponding rotationally securing flattened surfaces.

16. An orthopedic tool system comprised of:
an orthopedic tool handle having an inner handle cavity;
an orthopedic tool having a D-shaped shaft with a single partially flattened surface and a chamfer at the handle-engaging end of said shaft; and
an internal D-shaped orthopedic tool adapter comprising
an integrally machined collar assembly having a collar base portion, an internal D-shaped tool receiving channel and an internal tubular sliding portion, wherein said internal tubular sliding portion contains three securing ball apertures contoured on their inward facing edge to have a first smaller diameter and symmetrically arranged around said tubular sliding portion and a locking ball slot;
a driver assembly comprised of a driver base portion, an interior collar channel and a cylindrical interior handle-connecting portion having a locking ball aperture corresponding to said locking ball slot, wherein said interior collar channel has a tapered portion of interior surface near a front of said interior collar channel creating a narrower diameter near said front of said interior collar channel and a larger diameter near a rear of said interior collar channel and wherein said locking ball aperture is contoured on its inward facing edge to have a second smaller diameter;
wherein said internal tubular sliding portion of said collar assembly is slidingly engaged with said interior collar channel of said driver assembly such that said three securing ball apertures are aligned with said tapered portion of said interior collar channel;
three securing balls, each engaged with and freely rotatable in one of said securing ball apertures, wherein said tapered portion of said interior collar engaging channel secures said securing balls in said securing ball apertures and wherein said first smaller diameter is less than a diameter of said securing balls;
a locking ball engaged with and freely rotatable in said locking ball aperture and said locking ball slot, wherein said locking ball is secured in said locking ball aperture by a sleeve and wherein said second smaller diameter is less than a diameter of said locking ball;
a spring having an outer diameter which is smaller than a diameter of said interior collar channel allowing said spring to be inserted in said interior collar channel to provide an outward force on said collar assembly, wherein outward movement of said collar assembly is prevent by said locking ball engaging said locking ball slot; and a shaft stop assembly securing said spring within said interior collar channel, wherein said shaft stop assembly has a chamfer corresponding to said chamfer of said orthopedic tool;

wherein said internal D-shaped orthopedic tool adapter is secured in said inner handle cavity, wherein said orthopedic tool is removable within said internal D-shaped tool receiving channel, slidingly and rotationally secured by said securing balls engaging said D-shaped shaft and centrally secured by said chamfer on said D-shaped shaft engaging said chamfer on said shaft stop assembly.

17. The system of claim 16 wherein said inner handle cavity is threaded and said cylindrical interior handle-connecting portion has a corresponding threaded exterior surface.

18. The system of claim 16 wherein said handle is a ratcheting handle.

19. The system of claim 16 wherein said internal tubular sliding portion and said interior collar channel have at least two corresponding rotational securing flattened surfaces.

20. The system of claim 16 wherein inward force applied to said slidable collar assembly aligns said securing balls with said larger interior collar channel diameter to increase a diameter of said D-shaped to receiving channel and said locking ball engages an outer-most surface of said locking ball slot to prevent further inward movement of said collar assembly.

* * * * *